(12) United States Patent
Frayne

(10) Patent No.: US 7,691,631 B2
(45) Date of Patent: Apr. 6, 2010

(54) USE OF A MODIFIED PHOSPHATE FOR ENHANCING THE NATURAL MUTATION RATE IN BACTERIA AND MUTATING RECOMBINANT DNA PHAGE INSERTS

(75) Inventor: Elizabeth Gay Frayne, Diamond Bar, CA (US)

(73) Assignee: Frayne Consultants, Diamond Bar, CA (US)

( * ) Notice: Subject to any disclaimer, the term of this patent is extended or adjusted under 35 U.S.C. 154(b) by 723 days.

(21) Appl. No.: 10/760,156

(22) Filed: Jan. 20, 2004

(65) Prior Publication Data

US 2005/0130305 A1     Jun. 16, 2005

Related U.S. Application Data

(63) Continuation-in-part of application No. 10/007,489, filed on Dec. 5, 2001, now Pat. No. 7,125,982.

(51) Int. Cl.
*C12N 15/01* (2006.01)
*C12N 15/74* (2006.01)

(52) U.S. Cl. ....................... 435/442; 435/472

(58) Field of Classification Search ....................... None
See application file for complete search history.

(56) References Cited

OTHER PUBLICATIONS

Kunkel et al., Proc. Natl. Acad. Sci. USA, vol. 78, No. 11, pp. 6734-6738, Nov. 1981.*
Kunkel et. al. (1981) Deoxynucleoside [1-thio] triphosphates prevent proof reading during in vitro DNA synthesis PNAS 78:6734-6738.

* cited by examiner

*Primary Examiner*—Nancy Vogel

(57) ABSTRACT

Methods are presented for enhancing the natural mutation rate of micro-organisms, particularly bacteria via a modified phosphate. The novel metabolite inhibits DNA repair mechanisms in vivo resulting in a 100-200 hundred fold increase in the mutation rate of bacteria. The method yields viable cells and allows for the continuous selection of incremental traits.

The modified phosphate can also be used to randomly mutate specific genes. In particular, high rates of random mutagenesis can be readily achieved in vivo using recombinant DNA phage. The phage are amplified in mutator media containing the modified phosphate. The resultant phage can be further mutated by another round of infection and growth in mutator media. After two such rounds of amplification significant mutation rates are achieved such that each phage insert bears a novel mutation. The mutator media can also be used to mutagenize recombinant DNA plasmids in virtually any bacterial host.

3 Claims, 1 Drawing Sheet

FIG. 1 INCORPORATION OF THIO-PHOSPHATE INTO SINGLE-STRANDED AND/OR DOUBLE-STRANDED DNA
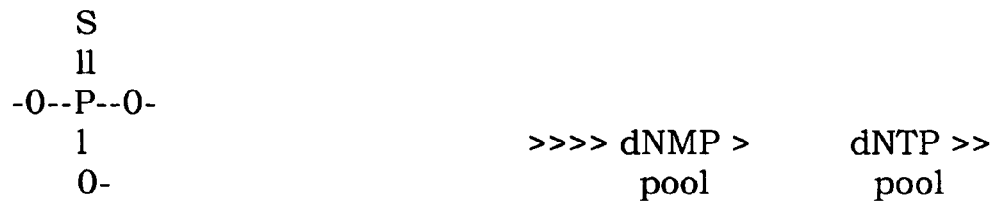
introduction
into feed source as
sole source of PO₄
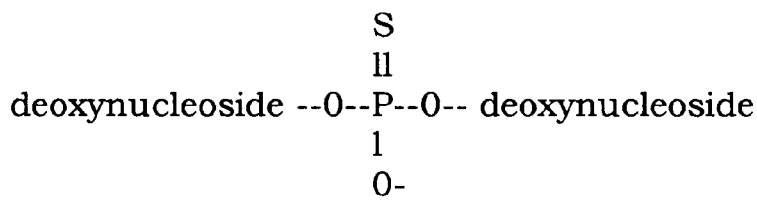
OR
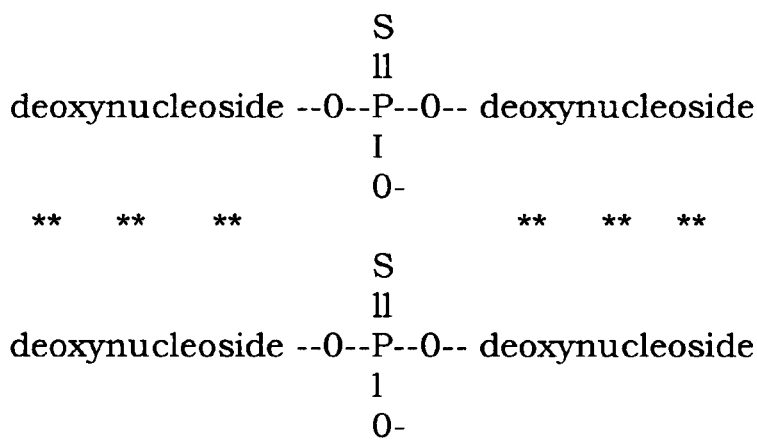
modified linkage in genomic, phage or plasmid DNA impairs
DNA editing by DNA polymerase and other repair mechanisms

USE OF A MODIFIED PHOSPHATE FOR ENHANCING THE NATURAL MUTATION RATE IN BACTERIA AND MUTATING RECOMBINANT DNA PHAGE INSERTS This application is a continuation-in-part of application Ser. No. 10/007,489, Filed Dec. 5, 2001, now U.S. Pat. No. 7,125,982 and related divisional application Ser. No. 10/679,305 (pending) and continued-in-part herein.

BACKGROUND OF THE INVENTION

1. Field of the Invention

The invention described herein provides a non-toxic method of increasing the natural mutation rate in bacteria. The method relies on the use of a modified salt namely thio-phosphate as a source of phosphate in culture media. Thio-phosphate is taken up by cells and ultimately incorporated into DNA such that it inhibits DNA editing and other cellular repair pathways. The mutation rate can be increased several hundred fold. Thio-phosphate substituted media is useful for generating variant strains, plasmids, or phage DNAs with high efficiency after several cycles of growth and amplification in thio-phosphate modified media.

2. Description of Related Disclosures

Traditional methods of mutagenesis involve chemical mutagens such as ethylmethane sulfonate (EMS) and others that are toxic carcinogens (Lawrence (1991) Methods and Enzymology 194:273-281). Such mutagens can be used to generate base substitutions, deletions, frame shift mutations, and additions. Another method of mutagenesis involves the use of transposable elements that when activated transpose and insert in or near a gene resulting in altered gene expression (Spradling (1999) Genetics 153:135; Rothstein (1991) Methods and Enzymology 194:281-301; Spradling and Rubin (1982) Science 218:341-347).

The mutagenesis of specific gene segments is an important tool in the field of biotechnology. Early work involved the chemical mutagenesis of recombinant DNA plasmids in vitro followed by transformation of cells in vivo (Sikorski and Boeke (1991) 194:302-318). More recent methods involve the use of mutator strains for growing plasmids (Greener et al (1996) Methods Mol. Biol. 57: 375-385) or in vitro mutagenesis of plasmids via error prone PCR (Cline et al (1996) NAR 24:3546-3551; Leung et al (1989) Technique 1; 11-15). A drawback of PCR mutagenesis has been a nonuniform mutational spectrum and low yields resulting from the required reaction conditions. Efforts to overcome such biases have been devised through the use of new enzymes (Cline and Hogrefe (2000) Strategies 13:157-161). Expanding the power of gene specific mutagenesis is the technique of PCR shuffling that is used to generate new combinations of mutant alleles for specific genes (Stemmer (1994) PNAS 91:10747-10751). The method involves the introduction of new mutations which serve as a source of genetic diversity for subsequent recombination events.

The present invention describes methods for the use of thio-phosphate as a mutagenic agent. Previous work has shown that phosphorothioate substituted DNA is resistant to DNA editing by DNA polymerase in vitro (Burgers and Eckstein (1979) J. Biol. Chem. 254:68896893). More recently, it has been shown (Frayne U.S. Ser. No. 10/007,489, Filed Dec. 5, 2001) that thio-phosphate can replace normal phosphate in cells and result in the incorporation of thio-phosphate nucleotides into DNA creating phosphorothioate linkages. Thus thio-phosphate can be used in culture media to increase the natural mutation rate by inhibiting DNA repair mechanisms in vivo. Cells can be grown for extended periods in media with thio-phosphate fully substituting for phosphate. The 100-200 fold increase in mutation rate is greater than the 20 fold increase expected from in vitro studies (Goodman et al (1993) Crit. Rev. Biochem. Mol. Biol. 28:83-126). Multiple repair pathways are presumably blocked by phosphorothioate linkages in bacteria. In contrast to bacteria yeast appear to show little or no increase in mutation rate when thio-phosphate is used as a source of phosphate in culture media. The enhanced mutation rate provides a novel means to mutate cells or recombinant DNA sequences in vivo and also allows for a wide range of mutations.

SUMMARY OF THE INVENTION

The present method of growing bacterial cells in 100% thio-phosphate substituted media provides an inexpensive and non-toxic method to increase the natural mutation rate for bacteria in general. This feature of the modified media should facilitate the generation of strains with new properties or useful DNA sequence variants for markers. It also has the advantage that cells can be grown under selective conditions when screening for phenotypes with an increased or decreased quantitative index.

The use of thio-phosphate for enhanced mutagenesis creates a mutator environment that can be used to efficiently mutate recombinant plasmid or phage DNA after two or more cycles of growth and amplification. The use of phage as a vector has the advantage that the DNA does not need to be purified after each cycle and instead only the phage supernatant needs to be retained for next round of amplification. The method described prevents mutations from accumulating in host cells and only viable phage DNAs are selected for. A significant mutation rate can be achieved without the use of error prone PCR suitable for directed evolution or protein structure and function studies. The use of recombinant DNA phage also provides a means to mutate entire collections of cloned DNA or cDNA libraries.

BRIEF DESCRIPTION OF THE DRAWINGS

FIG. 1. Depicts pathway for uptake of thio-phosphate by cells and incorporation into nucleic acids. The result is the creation of phosphorothioate linkages which are resistant to DNA editing and other repair mechanisms.

DESCRIPTION OF THE PREFERRED EMBODIMENTS

Thio-phosphate is readily metabolized by a variety of cell types (Frayne Ser. No. 10/007,489, Filed Dec. 5, 2001; Frayne U.S. division of Ser. No. 10/007,489, Filed Dec. 5, 2003). The modified phosphate is incorporated into dNTP and NTP precursor pools and ultimately nucleic acids. In doing so it impairs DNA repair mechanisms particularly in bacteria and can thus be used in general as a mutagenic agent for prokaryotic micro-organisms. Micro-organisms are used extensively in the production of various entities such as enzymes, antibiotics, chemicals, etc. Cultivation and maintenance of industrial strains is crucial to the outcome of such fermentation reactions. In addition, new strains are often developed to increase productivity.

Many commercially successful micro-organisms have been selected for years to achieve their desired properties. Generally such strains are subject to chemical or UV mutagenesis. These methods have limitations in the types of mutations generated. Critical for the maintenance of bacterial strains is a knowledge of the strain's mutation rate. The greater the mutation rate the greater the tendency for that strain to form substrains. Many factors can influence mutation rates and even different genes can have different mutation rates. The greater the scale of production the greater the need to minimize mutation rates as mutants will accumulate during scale up (Frayne (2002) American Biotechnology 21:68). It is useful to gather information about gene specific mutation rates to assess the overall mutation rate for a given strain. To reduce the number of bacteria required for screening one can examine the accumulation of mutations by serial dilution. A single colony will contain ~1 million cells indicating a 20 fold amplification. If this colony is picked, grown, and replated the number of mutations will increase 400 fold (20×20) above the mutation rate per generation. By growing cells in mutator medium or agar plates containing thio-phoshate, the number of mutations can be increased further approximately ~200 fold during each growth stage. This enables the screening of mutations after two to three cycles of plating and amplification. Different strains can then be compared to assess their relative mutation rates or to validate mutation rates.

Multiple rounds of amplification in mutator media and plating of individual colonies can be used to accelerate the accumulation of mutations. Only small volumes of media are required for growth or plating. The process also helps to select for viable cells. For example, it is possible to select for increased growth of an organism in the continued presence of mutator media. This may facilitate selection by allowing for the gradual accumulation of mutations under selective conditions in which growing cells are favored. Multiple rounds of growth and selection allow for a stepwise increase in growth rate. This type of approach is suitable for continuous traits and not discontinuous traits where a period in the absence of selection is required for the expression of the gene or genes leading to the new phenotype. However, cells can be plated on normal media which allows for the expression of genes in the absence of selection, after which it becomes possible to select for discontinuous traits.

For mutagenesis with thio-phosphate requiring extended culture periods it is best to prepare phosphate depleted nutrient broths to achieve high levels of thio-phosphate incorporation. This can be done by magnesium sulfate precipitation of phosphate in the presence of ammonium hydroxide (Rubin (1973) J. Biol. Chem. 248:3860). Bacterial cells respond well to high levels of thio-phosphate producing high yields of recombinant DNA molecules when grown in such medias.

Thio-phosphate mutator media can also be used for generating random mutations in specific genes. The method has the advantage that it can be done inexpensively in vivo for a large number of recombinant DNA molecules. There are two approaches that can be used depending on the particular situation. For recombinant DNA plasmids cells can be grown in mutator media designed for that organism (Frayne U.S. Ser. No. 10/007,489, Filed Dec. 5, 2001). After several cycles of plating and amplification in mutator media plasmids can be isolated and used to transform cells. Additional cycles of plating and amplification can be used if necessary. The limitation of this method comes from the viability of the host cell which will also accumulate mutations that are deleterious at a higher rate owing to its much larger complexity. That is why it is necessary to isolate the plasmid and start again with new host cells to increase the mutation rate to the desired level.

To mutate specific genes it is best to use phage DNA as the phage can easily be separated from host cells and used in successive rounds of mutagenesis. In contrast to plasmids the limitation of phage mutagenesis arises not from host cell viability but rather from the size of the virus used. The procedure selects for viable phage and the smaller the phage the better as fewer genes will be required for successful infections. Recombinant M13 phage works quite well and it is possible to obtain a high rate of mutagenesis of the recombinant DNA insert targeted (~one to two mutations per insert). It is also conceivable that libraries of recombinant phage can be collectively mutated. Mutagenesis of this type is useful for directed evolution.

EXPERIMENTAL

Example I

Random Mutagenesis of M13 Recombinant DNA Phage

Recombinant M13 phage DNA can be mutated at a high rate by amplification in thio-phosphate containing media. The propagation of M13 phage in thio-phosphate containing media first requires the cultivation of the appropriate host strain such as JM109 which requires minimal media to select for the F' pillus. Minimal plates are prepared as follows: bactoagar, 10.5 g/L; $K_2HPO_4 3H_2O$, 4.5 g/L; $KH_2PO_4$, 4.5 g/L; $(NH_4)_2SO_4$, 1 g/L; sodium citrate $2H_2O$, 0.5 g/L; Adjust pH to 7.4 and autoclave. Then add the following: $MgSO_4 7H_2O$, 0.2 g/L (sterilized separately as a conc. solution); (thiamine HCL, 5 ug/L; glucose, 4 g/L sterilized separately by filtration). Glucose can also be sterilized by autoclaving separately. $FeCl_2$ (500 ug/L) can also be added as needed. Thio-phosphate containing media is prepared similarly as minimal media except that the inorganic phosphates are replaced with thio-phosphate ($Na_3SPO_3XH_2O$) 10-15 g/L and KCL (1.5 g/L). Thio-phosphate contains variable amounts of water (10-15 per molecule) not included in molecular weight calculations. It is almost 50% water by weight. Note pH control is important in maximizing thio-phosphate stability. To ensure adequate growth, use a high density innoculum. The preferred pH is neutral or slightly basic. Alternatively as described above phosphate depleted nutrient broth can be used and thio-phosphate added at ~1 g per liter.

Several media are required for the production of infectious phage particles: LBM medium (bacto tryptone, 10 g/L; bacto yeast extract, 5 g/L; NaCl, 5 g/L; 2 g/L $MgCl_2H_2O$; 10 mM Tris/HCL pH 7.5. LBM agar plates (add 15 gm Bacto-agar to 1 liter of LBM medium and autoclave); soft agar (add 7 gm of bacto-agar to 1 liter of LBM medium. Store at 4° C. and heat to 45° C. before use.).

Phage are generated by transforming JM109 cells with the replicative form of M13 DNA or double-stranded DNA using the calcium chloride (Dagert and Ehrlich (1979) Gene 6:23) or DMSO/PEG (Chung et al (1989) PNAS 86:2172-2176). The transformed cells produce infectious particles when grown in nutrient broth. To 0.3 ml of competent cells add 5 ng of DNA and let the mixture sit on ice for 40 min. Then heat shock the cells at 42° C. for 2 min. and add the following: 0.2 ml of fresh JM109 cells and 3 ml of top agar at 45° C. Mix and plate directly onto LBM plates. Let the plates solidify and then incubate at 37° C. until plaques are seen (overnight). The plaques appear as turbid clearings on the bacterial lawn. A plaque can then be picked with a sterile toothpick and used to innoculate 2 ml of LBM broth and grown with shaking overnight. The cells are spun out and the supernatant is saved as phage stock at 4° C. The supernatant (20 ul) can be run directly on a gel to test for the presence of DNA. The titer of the stock should be checked to ensure high yields. The titer should be at least $1 \times 10^{10}$/ml.

To prepare phosphorothioate phage substituted DNA, JM109 cells are incubated overnight in LB broth. The starter culture can be used directly. Generally 500 ml of thio-phosphate containing media are innoculated with 10-25 ml of overnight culture (high density) and grown for ~1.5 hrs to an OD 600=0.3 (early log phase). At this point infect cells with phage stock at a moi of 1 pfu per 10 bacterial cells. This corresponds to approximately 500 ul of phage stock. The cells are then incubated at 37° C. with shaking for 3 hr. and not more.

Mutation rates are assayed easily by scoring plaques for beta-galactosidase activity using a standard blue/white colormetric assay involving IPTG (isopropyl-beta-D-thiogalactopyranoside) and X-gal (5-bromo-4-chloro-3-indolyl-beta-D-galactoside). To assay for activity, an aliqout of phage is mixed with 0.2 ml of JM109 cells, 10 ul IPTG (100 mM), and 50 ul Xgal (2%). Three mls of top agar are added and the entire mixture with phage is plated on 1X YT (bacto tryptone, 8 g/L; bacto yeast extract, 10 g/L; NaCl, 10 g/L. Adjust pH to 7.5) plates and incubated overnight. Wildtype plaques are blue and those with mutations are colorless. After one round of phage amplification in thio-phosphate media, the bacterial cells are spun out and the supernatant assayed for colorless plaques. The phage containing supernatant is plated such that ~1000 plaques are formed per plate; the titer is similar for wildtype and phosphorothioate phage after one round of amplification. For phosphorothioate DNA phage approximately two mutant plaques are observed per plate or 1/400. Wildtype phage grown for the same period do not generate mutants (less than 1/4000). The percentage of mutants observed can be increased by another round of amplification in thio-phosphate media. The phosphorothioate DNA phage from the first amplification are used to innoculate the second round of amplification. The phage supernatant from the second round of amplification has a lower titre (~five fold) than that of similarly prepared wildtype phage. Nevertheless, the mutation rate is quite high, on the order of 1/6 compared with wildtype phage grown under similar conditions (<1/1000). The fold enhancement (~>200) of the mutation rate is much greater than expected from in vitro studies (20 fold) indicating that multiple repair mechanisms are inhibited (Kunkel et al (1981) PNAS 78:6734-6738). Note that the assay used measures enzyme activity and does not include silent or missense mutations that do not disrupt enzyme activity. Therefore, the real mutation rate is actually higher and more in the range of one to two mutants per phage DNA insert.

Example II

Method of Enhancing the Natural Rate of Mutagenesis

*S. cerevisiae* grown in thio-phosphate media (phosphate free minimal media, EMM supplemented with SP (Bio101) and 1 g/L thio-phosphate) also exhibit an enhanced mutation rate though much less so than observed in bacteria. To test the mutation rate yeast cells were selected for canavanine resistance (60 ug/ml) in minimal media minus arginine (Hoffman (1985) J. Biol. Chem. 260:11831-11836) and 100% thio-phosphate. An overnight culture of the haploid yeast strain ATTC 32119 was used to innoculate thio-phosphate media at a one to twenty volume ratio. The number of viable yeast cells after one to two days of growth at 30° C. is reduced compared to wildtype when tested on normal phosphate containing plates. The yeast are pelleted by centrifugation and washed with water and resuspended in water at the original volume. The resuspended cells are then spread (~50 ul 100 mm plate) on canavanine containing plates and Can$^R$ colonies observed after two days as distinct colonies. The average increase in mutation rate for yeast grown in thio-phosphate media compared to normal media is approximately 10 fold (range observed 3.9-18.5).

What is claimed is:

1. A method for enhancing the natural rate of mutagenesis in bacteria by
   1) growing bacteria in media utilizing thio-phosphate as a source of phosphate to create phosphorothioate linkages in genomic DNA which thereby impair DNA editing and repair pathways in the cell
   2) allowing mutations to accumulate to the desired level by performing multiple rounds of bacterial growth and amplification in mutator media either by serial dilution into liquid mutator broth and/or by plating individual colonies onto solid agar plates containing thio-phosphate.

2. A method to facilitate the mutagenesis of recombinant phage DNAs and/or phage DNA libraries comprising:
   1) growing bacterial host cells in media containing thio-phosphate as a source of phosphate
   2) infecting recombinant phage at a suitable multiplicity of infection into the growing bacterial culture
   3) continued culture and replication of the recombinant phage in the host cell culture such that the phage genome is modified with phosphorothioate linkages to inhibit DNA repair and editing of the phage during replication in the cell followed by isolation of intact phage particles
   4) repeating steps 1-3 using the now chemically modified recombinant phage and fresh host cells until the desired level of mutagenesis is achieved.

3. A method to facilitate the mutagenesis of recombinant plasmid DNA and/or plasmid DNA libraries as follows:
   1) growing bacteria transfected with a recombinant plasmid DNA in media containing thio-phosphate as a source of phosphate to create phosphorothioate linkages in the recombinant plasmid DNA which inhibit DNA repair and editing of the plasmid during replication in the cell
   2) isolating the recombinant plasmid DNA from the bacterial culture after the culture becomes saturated
   3) transforming fresh bacteria with the now chemically modified recombinant plasmid DNA
   4) repeating steps 1-3 until the desired level of mutagenesis is achieved.

* * * * *